(12) United States Patent
Ueno

(10) Patent No.: US 6,291,521 B1
(45) Date of Patent: Sep. 18, 2001

(54) ANTI-PORTAL HYPERTENSIVE AGENT

(75) Inventor: Ryuji Ueno, Montgomery, MD (US)

(73) Assignee: R-Tech Ueno, Ltd., Osaka (JP)

(*) Notice: Subject to any disclaimer, the term of this patent is extended or adjusted under 35 U.S.C. 154(b) by 0 days.

(21) Appl. No.: 09/319,868

(22) PCT Filed: Sep. 30, 1998

(86) PCT No.: PCT/JP98/04398

§ 371 Date: Jun. 14, 1999

§ 102(e) Date: Jun. 14, 1999

(87) PCT Pub. No.: WO99/18968

PCT Pub. Date: Apr. 22, 1999

(30) Foreign Application Priority Data

Oct. 13, 1997 (JP) .................................................. 9-278539

(51) Int. Cl.$^7$ ...................... A61K 31/557; A61K 31/215; A61K 31/19
(52) U.S. Cl. ........................ 514/530; 514/573; 514/570; 514/571; 514/690; 514/893
(58) Field of Search .................................... 514/530, 573, 514/570, 571, 690, 893

(56) References Cited

U.S. PATENT DOCUMENTS 5,096,927 * 3/1992 Ueno et al. ........................ 514/530

* cited by examiner

Primary Examiner—Frederick Krass
(74) Attorney, Agent, or Firm—Sughrue, Mion, Zinn, Macpeak & Seas, PLLC

(57) ABSTRACT

The present invention provides an anti-portal hypertensive agent comprising a 15-keto-prostaglandin compound as an active ingredient.

10 Claims, No Drawings

ANTI-PORTAL HYPERTENSIVE AGENT

This application is a 371 of PCT/JP98/04398, filed Sep. 30, 1998.

TECHNICAL FIELD

The present invention provides a novel use of 15-keto prostaglandins as an anti-portal hypertensive agent.

The agent of the present invention is useful for treatment of portal hypertension.

BACKGROUND ART

Portal hypertension is a disease state characterized by increased portal blood flow resistance and increased portal vein pressure due to occlusion or congestion of portal or hepatic venous system. Factors, which may contribute to the etiology of this state may be classified into pre sinusoidal and post sinusoidal conditions. The pre sinusoidal conditions include portal vein thrombosis, oriental schistosomiasis and Hodgkin's disease; and the post sinusoidal conditions include hepatocirrhosis, wedged hepatic venous occlusive disease and congestive heart disease.

The term "portal vein system" is a part of blood system wherein a vein or group of veins are branched to form a network of capillaries, and the capillaries then merge to form a vein or group of veins. In human beings, there are hepatic portal vein system and hypophyseal portal vein system, and in the hepatic portal vein system, splenic vein and superior and inferior mesenteric veins merge to form said system.

Prostaglandins (hereinafter, referred to as PG(s)) are members of class of organic carboxylic acids, which are contained in tissues or organs of human or most other mammalian, and exhibit a wide range of physiological activity. PGs found in nature (primary PGs) generally have a prostanoic acid skeleton as shown in the formula (A):

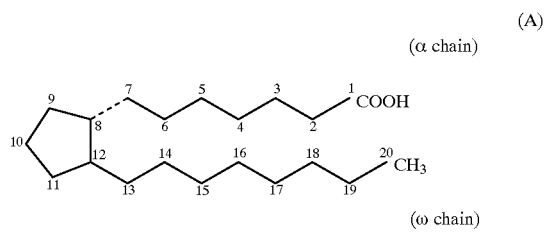

(A)
(α chain)
(ω chain)

On the other hand, some of synthetic analogues have a modified skeleton. The primary PGs are classified to PGAs, PGBs, PGCs, PGDs, PGEs, PGFs, PGGs, PGHs, PGIs and PGJs according to the structure of the five-membered ring moiety, and named hereafter the existence or non-existence of an unsaturated bond or an oxidized group at the carbon chain moiety:

subscript 1: 13,14-unsaturated-15-OH subscript 2: 5,6- and 13,14-diunsaturated-15-OH subscript 3: 5,6-, 13,14-, and 17,18-triunsaturated-15-OH.

Further, the PGFs are classified, according to the configuration of the hydroxyl group at the 9-position) into α type (the hydroxyl group is of an α-configuration) and α type (the hydroxyl group is of a β-configuration).

In addition, some 15-keto (i.e. having an oxo group at position 15 in place of the hydroxy group) prostaglandins and 13,14-dihydro-15-keto-prostaglandins are known as substances naturally produced by enzymatic actions during metabolism of primary PGs. 15-keto PGs have been disclosed in, for example, EP-A-0281239 (corresponds to JP-A-104040/89), EP-A-0281480 (corresponds to JP-A-52753/89), EP-A0289349 (corresponds to JP-A-151552/89), and EP-A-0690049 (corresponds to JP-A-48665/96).

It is well known in the art that PG derivatives affect blood pressure. For example, PGE1, one of the primary PGs, has been known to have blood pressure decreasing activity, whereas 15-keto PGs have blood pressure increasing activity. However, the term "blood pressure" is generally used for "arterial blood pressure", and therefore, the effect of PGs, which have some activity in "arterial blood pressure", on pressure of portal vein system which consisting of venous vascular system is quite unpredictable.

As to the effects of PGs on portal vein pressure, PGE1 and PGE2, primary PGs, have been reported to have some effect. However, there are inconsistent evaluation among the reports such that increased, decreased and unchanged of the pressure due to the PGs were disclosed in the different reports. It has not been reported that how 15-keto-prostaglandin compounds affect portal vein pressure.

SUMMARY OF THE INVENTION

An object of the invention is to provide an anti-portal hypertensive agent useful for treatment to suppress increased portal vein pressure that occurs due to various factors and accomplished the present invention.

As a result of extensive studies about the biological properties of 15-keto-PG compounds, the present inventor has discovered that these compounds have anti-portal hypertensive activity.

That is, the present invention provides an anti-portal hypertensive agent comprising a PG compound as an active ingredient.

In the present invention, "15-keto-Prostagrandin compounds (hereinafter, referred as 15-keto-PG compounds)" include any of derivatives or substituted derivatives of a compound having an oxo group at 15-position of the prostanoic acid skeleton instead of the hydroxy group, irrespective to the configuration of the 5-memberd ring, or number of double bonds, presence or absence of a substituent or any other modification in the α or ω chain.

Nomenclature of 15-keto-PG compounds herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms. Carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in the order starting from position 2; and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20; and when the number of carbon atoms is increased in the ω-chain, compounds are named as substituted derivatives having respective substituents at position 20. Stereochemistry of the compounds is the same as that of above formula (A) unless otherwise specified.

In general, PGDs, PGEs and PGFs represent a compound having hydroxy groups at positions 9 and/or 11, and in the present specification they also include PGs having substituents other than hydroxyl group at positions 9 and/or 11. Such compounds are referred to as 9-dehydroxy-9-substituted-PG compounds or 11-dehydroxy-11-substituted-PG compounds. In case of having hydrogen in place of hydroxy group, it is simply named as 9 or 11-dehydroxy compound.

As stated above, nomenclature of 15-keto-PG compounds is based upon the prostanoic acid skeleton. However, in case the compound has a similar partial construction as a prostaglandin, the abbreviation of "PG" may be used. Thus, a 15-keto-PG compound of which ω-chain is extended by two carbon atoms, that is, having 10 carbon atoms in the ω-chain is nominated as 15-keto-20-ethyl-PG. These compounds, however, can also be named according to the IUPAC naming system.

According to the IUPAC naming system, for example, 13,14-dihydro-15-keto-16R,S-fluoro-PGE$_2$ is (Z)-7-{(1R,2R,3R)-3-hydroxy-2-[(4R,S)-fluoro-3-oxo-1-octyl]-5-oxocyclopentyl}-hept-5-enoic acid; 13,14-dihydro-15-keto-20-ethyl-11-dehydroxy-11R-methyl-PGE$_2$ methyl ester is methyl 7-{(1R,2S,3S)-3-methyl-2-[3-oxo-1-decyl]-5-oxocyclopentyl}-hept-5-enoate; and 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxocyclopentyl}-6-oxo-heptanoate. 13,14-dihydro-15-keto-20-ethyl-PGF$_2\alpha$ isopropyl ester is isopropyl (Z)-7-[(1R,2R,3R,5S)-3,5-dihydro-2-{3-oxo-1-decyl)-cyclopentyl]-hept-5-enoate; and 13,14-dihydro-15-keto-20-methyl-PGF$_2\alpha$ methyl ester is methyl (Z)-7-[(1R,2R,3R,5S)-3,5-dihydroxy-2-{3-oxo-1-nonyl}-cyclopentyl]-hept-5-enonate.

The 15-keto-PG compounds used in the present invention may be any derivatives of PG insofar as they have an oxo group at position 15 in place of the hydroxy group, and may have a double bond between positions 13 and 14 (15-keto-PG type 1 compounds), two double bonds between positions 13 and 14 as well as positions 5 and 6 (15-keto-PG type 2 compounds), or three double bonds between positions 13 and 14, positions 5 and 6 as well as positions 17 and 18 (15-keto-PG type 3 compounds), and may have a single bond between positions 13 and 14 (13,14-dihydro-1 5-keto-PG compounds).

Typical examples of the compounds used in the present invention include 15-keto-PG type 1, 15-keto-PG type 2, 15-keto-PG type 3, 13,14-dihydro-15-keto-PG type 1, 13,14-dihydro-15-keto-PG type 2, 13,14-dihydro-15-keto-PG type 3 and the derivatives thereof.

Examples of substitution products or derivatives of the above compounds include a compound of which the carboxy group at the end of alpha chain is esterified; physiologically acceptable salts; unsaturated derivatives having a double bond between positions 2 and 3 or a triple bond between positions 5 and 6; substituted derivatives having substituent (s) on carbon atom(s) at position(s) 3, 5, 6, 16, 17, 18, 19 and/or 20; and compounds having lower alkyl or a hydroxy (lower) alkyl group at position 9 and/or 11 in place of the hydroxy group, of the above PGs.

According to the present invention, preferred substituents on the carbon atom at position 3, 17 and/or 19 include alkyl having 1–4 carbon atoms, especially methyl and ethyl. Preferred substituents on the carbon atom at position 16 include lower alkyl, such as methyl and ethyl, hydroxy, halogen atom, such as chlorine and fluorine, and aryloxy, such as trifluoromethylphenoxy. Preferred substituents on the carbon atom at position 17 include halogen atom, such as chlorine and fluorine. Preferred substituents on the carbon atom at position 20 include saturated and unsaturated lower alkyl, such as $C_{1-4}$ alkyl, lower alkoxy, such as $C_{1-4}$ alkoxy, and lower alkoxy alkyl, such as $C_{1-4}$ alkoxy-$C_{1-4}$ alkyl. Preferred substituents on the carbon atom at position 5 include halogen atom, such as chlorine and fluorine. Preferred substituents on the carbon atom at position 6 include an oxo group forming a carbonyl group. Stereochemistry of PGs having hydroxy, lower alkyl or lower(hydroxy)alkyl substituent on the carbon atom at positions 9 and 11 may be α, β or mixtures thereof.

Said derivatives may further have an alkoxy, phenoxy or phenyl group at the end of the omega chain where the chain is shorter than the primary PGs.

Especially preferred compounds include 13,14-dihydro-15-keto-PG compounds that having a single bond between positions 13 and 14; 15-keto-16 mono or di-halogen PG compounds that having one or two halogen atoms, such as chlorine and fluorine, at position 16; 15-keto-PGE compounds that having an oxo group at position 9 and a hydroxy group at position 11 of the five memberd ring.

A group of preferred compounds used in the present invention has the formula (I):

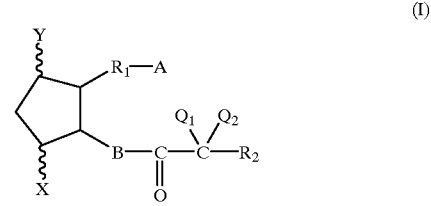

wherein X and Y are hydrogen, hydroxy, halogen, lower alkyl, hydroxy(lower)alkyl, or oxo, with the proviso that at least one of X and Y is a group other than hydrogen, and the 5-membered ring may have at least one double bond;

A is —CH$_2$OH, —COCH$_2$OH, —COOH or a functional derivative thereof;

B is —CH$_2$—CH$_2$—, —CH=CH— or —C≡C—;

Q$_1$ and Q$_2$ are hydrogen, halogen or lower alkyl;

R$_1$ is bivalent saturated or unsaturated, lower or medium aliphatic hydrocarbon residue which is unsubstituted or substituted with halogen, oxo or aryl;

R$_2$ is saturated or unsaturated, lower or medium aliphatic hydrocarbon residue which is unsubstituted or substituted with halogen, oxo, hydroxy, lower alkoxy, lower alkanoyloxy, cyclo lower alkyl, aryl or aryloxy.

In the above formula, the term "unsaturated" in the definitions for R$_1$ and R$_2$ is intended to include at least one and optionally more than one double bond and/or triple bond that are isolatedly, separately or serially present between carbon atoms of the main and/or side chains. According to the usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarbyl group having 1 to 14 carbon atoms (for a side chain, 1 to 3 carbon atoms are preferred) and preferably 4 to 10, especially 6 to 8 carbon atoms for R$_1$ and 1 to 10, especially 2 to 8 carbon atoms for R$_2$.

The term "halogen" denotes fluoro, chloro, bromo and iodo.

The term "lower" throughout the specification is intended to include a group having 1 to 6 carbon atoms unless otherwise specified.

The term "lower alkyl" refers to saturated and straight or branched chain hydrocarbon groups containing 1 to 6 carbon atoms and includes, for example, methyl, ethyl, propyl, isopropyl, butyl, isobutyl, t-butyl, pentyl and hexyl.

The term "lower alkoxy" refers to the group of lower-alkyl-O—, wherein lower alkyl is as defined above.

The term "hydroxy(lower)alkyl" refers to lower alkyl as defined above which is substituted with at least one hydroxy group, such as hydroxymethyl, 1-hydroxyethyl, 2-hydroxyethyl and 1-methyl-1-hydroxyethyl.

The term "lower alkanoyloxy" refers to a group of the formula: RCO—O—, wherein RCO— is an acyl group formed by oxidation of a lower alkyl group as defined above, such as acetyl.

The term "cycloloweralkyl" refers to a cyclic group formed by cyclization of a lower alkyl group as defined above but contains three or more carbon atoms as defined above, and includes, for example, cyclopropyl, cyclopentyl and cyclohexyl.

The term "aryl" includes unsubstituted or substituted aromatic carbocyclic or heterocyclic (preferably monocyclic) groups, for example, phenyl, tolyl, xylyl and thienyl. Examples of the substituents are halogen, and halo(lower)alkyl wherein halogen, and lower alkyl being as defined above.

The term "aryloxy" refers to a group of the formula: ArO—, wherein Ar is aryl as defined above.

The term "functional derivative" of carboxy as A includes salts (preferably pharmaceutically acceptable salts), esters and amides.

Suitable "pharmaceutically acceptable salts" include conventional non-toxic salts, and may be a salt with an inorganic base, for example an alkali metal salt (such as sodium salt and potassium salt) and an alkaline earth metal salt (such as calcium salt and magnesium salt), ammonium salt, a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by the conventional process, for example from the corresponding acid and base or by salt interchange.

Examples of the esters include aliphatic esters, for example, lower alkyl ester, such as methyl ester, ethyl ester, propyl ester, isopropyl ester, butyl ester, isobutyl ester, t-butyl ester, pentyl ester and 1-cyclopropylethyl ester; lower alkenyl ester, such as vinyl ester and allyl ester; lower alkynyl ester, such as ethynyl ester and propynyl ester; hydroxy(lower)alkyl ester such as hydroxyethyl ester; lower alkoxy(lower)alkyl ester, such as methoxymethyl ester and 1-methoxyethyl ester; aromatic esters, for example optionally substituted aryl ester such as phenyl ester, tosyl ester, t-butylphenyl ester, salicyl ester, 3,4-di-methoxyphenyl ester and benzamidophenyl ester; and aryl(lower)alkyl ester such as benzyl ester, trityl ester and benzhydryl ester. Examples of the amides are mono- or di-lower alkyl amides, such as methylamide, ethylamide and dimethylamide; arylamide, such as anilide and toluidide; and lower alkyl- or aryl-sulfonylamide, such as methylsulfonylamide, ethylsulfonyl-amide and tolylsulfonylamide.

Preferred examples of X and Y include hydroxy and oxo, and especially, X is hydroxy and Y is oxo which has a 5-membered ring structure of, so called, PGE type.

Preferred examples of A include —COOH, and a pharmaceutically acceptable salt or ester amide thereof.

Preferred example of B is —$CH_2$—$CH_2$— and having the structure of, so called, 13,14-dihydro type.

Preferred example of $Q_1$ and $Q_2$ is that at least one of them is halogen, more preferably, both of them are halogen, especially, fluoro and having a structure of, so called, 16,16-fluoro type.

Preferred $R_1$ is hydrocarbon containing 4–10 carbon atoms, especially, 6–8 carbon atoms.

Preferred $R_2$ is hydrocarbon containing 1–10 carbon atoms, especially, 2–8 carbon atoms and further that having one or two side chain consisting of one carbon atom.

The configuration of the ring and the α- and/or ω chain in the above formula (I) may be the same as or different from that in the primary PGs. However, the present invention also includes a mixture of a compound having a primary configuration and that of an non-primary compound.

Examples of the typical compounds of the present invention are 13,14-dihydro-15-keto-16-mono or di fluoro-PGE compounds and derivatives thereof.

When a 15-keto-PG compound of the present invention has a saturated bond between positions 13 and 14, these compound may be in the keto-hemiacetal equilibrium by forming a hemiacetal between hydroxy at position 11 and keto at position 15.

The proportion of both tautomeric isomers, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend to eliminate the hemiacetal type of compounds.

According to the present invention, any of the individual tautomeric isomers, a mixture thereof, or optical isomers, a mixture thereof, a racemic mixture, and other isomers such as steric isomers may be used in the same purpose.

Some of the compounds used in the present invention may be prepared by the method disclosed in EP-A-0281239 (corresponds to JP-A-52753/1989), EP-A-0284180 (corresponds to JP-A-104040/1989), EP-A-0289349 (corresponds to JP-A-151519/1989), and EP-A-0690049 (corresponds to JP-A-48665/96). Alternatively, these compounds may be prepared by a process analogous to that described herein or to any process known in the art.

Since the 15-keto-PG compounds described as above have an anti-portal hypertensive activity, said compounds are useful for treatment of portal hypertension induced by various factors.

As used herein, the term "treatment" or "treating" refers to any means of control of a condition, including prevention, cure and relief of the condition and arrestation or relief of development of the condition.

Such activities can be determined by a standard method such as a method using portal hypertensive rats (rat portal vein-ligated model).

The agent of the present invention may be used as a pharmaceutical composition for animals and human beings. The composition are usually applied systemically or topically by such methods as oral administration, intravenous injection (including instillation), subcutaneous injection, or rectal or vaginal suppository administration and the like. While the dosage may vary depending on the animal or human to be treated, such as age, body weight, condition to be treated, desired therapeutic effect, administration route, term of treatment and the like, the dosage may be around 0.001–100 mg/kg for systemic administration in 2 to 4 divided doses per day or for sustained administration.

The anti-portal hypertensive agent of the present invention may be formulated as a pharmaceutical composition for oral administration, injection, infusion or external administration, tablet, sublingual tablet or rectal or vaginal suppository and the like.

These compositions may further contain physiologically acceptable additives. According to the present specification, the term "additives" represents any ingredients of the pharmaceutical composition used with 15-keto-prostagrandin compounds, such as excipient, diluent, extender, solvent, smoothing agent, lubricant, adjuvant, binder, disintegrator, capuslating agent, ointoment basis, suppository basis, aerosol, emulsifier, dispersing agent, suspensing agent, viscosity increasing agent, isotonic agent, buffer, painless agent, preservative agent, antioxidant, flavoring agent, odor improving agent, flavor, coloring agent, functional material such as cyclodextrins or biodegradable polymer. An appropriate additive may be selected based on standard books known in the art relating preparation of medicine.

According to the present invention, the amount of 15-keto-prostaglandin compound in the composition may vary based on the formulation of the compound, and normally, it may be 0.0001–10.0 weight %, more preferably, 0.001–10.0 weight %.

The solid composition for oral administration used according to the invention includes tablets, troches, capsules, pills, powders, granules and the like. The solid composition may contain one or more active substances in admixture with at least one inactive diluent. The composition may also contain conventional additives, for example, lubricants, disintegrator and stabilizers. Tablets or pills may be gastric- or enteric-coated preparation, may be that formed by adsorbing the active ingredient to a material which allows sustained release of the ingredient, or may be in the form of micro-capsules. Further, it may be coated with two or more layers. Liquid compositions for oral administration may be liquid preparation, emulsions, suspensions, syrups, elixirs and the like. Such a preparation may contain conventional inactive diluent such as purified water or ethanol. The composition may contain adjuvant other than the inactive diluent, such as wetting agents and suspending agents, sweeteners, flavors, perfumes and preservatives.

An injectable preparation of this invention for parenteral administration may include sterile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oil and ethanol. The composition may contain other additives, such as preservatives, wetting agents, emulsifying agents, dispersing agents and the like. These are sterilized by, for example, filtration through a bacteria-retaining filter, compounding with a sterilizer, gas or radiation sterilization. The injectable preparation may also be prepared from sterilized solid composition by dissolving in a sterilized solvent for injection at the use.

Another formulation according to the present invention is a rectal or vaginal suppository. This may be prepared by mixing the active compound according to the invention with a suppository base, which is softened at body temperature.

BEST MODES FOR CARRYING OUT THE INVENTION

A more complete understanding of the present invention will be obtained by reference to the following Test Examples. These examples are provided for the purpose of illustration only and are not intended to limit the scope of the invention by any meaning.

TEST EXAMPLE

Effect of 15-keto-PG on Portal Hypertensive Rat (Rat Portal Vein Ligated Model)

As the test animals, male SD rats were used. Under ether anesthesia, abdominal skin of the rat was incised along the median line and the portal vein in the hepatic portal vein system was exposed. A blunt ended 20-gauge needle was placed along with the longitudinal direction of the portal vein, and the portal vein was ligated together with the needle at the position between the left and the right portal veins are merged with 3-0 silk ligature. Then, the needle was removed, the abdomen was closed to provide a portal-hypertensive rat. After two or three weeks from the surgery, the animal was fasted for 16 hours and then, catheter was inserted in the superior mesenteric vein (ileac vein) at the bifurcation and fixed there. The catheter was connected to a pressure gauge transducer to monitor the portal vein pressure. The test compounds were administrated in duodenum via a catheter induced and fixed there.

Result

Result is shown in the following table. The values in the table show the difference of the portal vein pressure between before and after administration of the compound ($\Delta$value$\pm$S.E. mmHg). As shown in the result, a significant portal-hypotensive activity was observed in the rat-portal hypertensive model by administering 10 $\mu$g/kg of the test-compound.

| test compound | dose $\mu$g/kg | animals n | time after administration(min) | |
|---|---|---|---|---|
| | | | 30 | 60 |
| 1 | 10 | 3 | −1.3 ± 0.1** | −1.0 ± 0.4* |

**<0.01
*<0.05 (compared with the value before the administration; Dunnet-t test)
Test compound 1: 13,14-dihydro-15-keto-16,16-difluoro-18S-methyl-prostaglandin E1

INDUSTRIAL APPLICABILITY

Since the anti-portal hypertensive agent of the present invention has an intensive anti-portal hypertensive activity, it is useful for treatment of portal hypertension, which may occur from various factors.

As used herein, the term "treatment" or "treating" refers to any means of control of a condition, including prevention, cure and relief of the condition and arrestation or relief of development of the condition.

What is claimed is:
1. A method for treating presinusoidal portal vein hypertension, which comprises administering to a patient in need of such treatment an amount of a 15-keto-prostaglandin compound effective for treating presinusoidal portal vein hyptertension.

2. The method of claim 1, wherein the 15-keto-prostaglandin compound is a compound of formula (I):

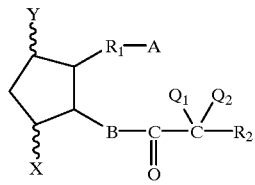

(I)

wherein

X and Y are hydrogen, hydroxy, halogen, lower alkyl, hydroxy(lower)alkyl, or oxo, with the proviso that at least one of X and Y is a group other than hydrogen, and the 5-membered ring may have at least one double bond;

A is —CH$_2$OH, —COCH$_2$OH, —COOH or a functional derivative thereof;

B is —CH$_2$—CH$_2$—, —CH=CH— or —C≡C—;

Q$_1$ and Q$_2$ are hydrogen, halogen or lower alkyl;

R$_1$ is bivalent saturated or unsaturated, lower or medium aliphatic hydrocarbon residue which is unsubstituted or substituted with halogen, oxo or aryl;

R$_2$ is saturated or unsaturated, lower or medium aliphatic hydrocarbon residue which is unsubstituted or substituted with halogen, oxo, hydroxy, lower alkoxy, lower alkanoyloxy, cyclo lower alkyl, aryl or aryloxy.

3. The method of claim 1, wherein the 15-keto-prostaglandin compound is a 13,14-dihydro-15-keto-prostaglandin compound.

4. The method of claim 1, wherein the 15-keto-prostaglandin compound is a 15-keto-16-mono- or di-halogen-prostaglandin compound.

5. The method of claim 1, wherein the 15-keto-prostaglandin compound is a 13,14-dihydro-15-keto-16-mono- or di-halogen prostaglandin compound.

6. The method of claim 1, wherein the 15-keto-prostaglandin compound is a 15-keto-16-mono- or di-fluoro prostaglandin compound.

7. The method of claim 1, wherein the 15-keto-prostaglandin compound is a 13,14-dihydro-15-keto-16-mono- or di-fluoro prostaglandin compound.

8. The method of claim 1, wherein the 15-keto-prostaglandin compound is a 15-keto-prostaglandin E compound.

9. The method of claim 1, wherein the 15-keto-prostaglandin compound is 13,14-dihydro-15-keto-16,16-difluoro-18-methyl prostaglandin E1.

10. The method of claim 1, which comprises administrating a 15-keto-prostaglandin compound at an amount of 0.001 to 100 mg/kg for 2 to 4 times per day.

* * * * *